United States Patent [19]

Hammond et al.

[11] Patent Number: 5,714,364
[45] Date of Patent: Feb. 3, 1998

[54] PHENYLALANINE DEHYDROGENASE PRODUCTION

[75] Inventors: Peter Michael Hammond, Salisbury, United Kingdom; Graham Mark Brearley, 1000 Oaks, Calif.; Christopher Philip Price, Stapleford, Great Britain

[73] Assignee: Microbiological Research Authority, Salisbury, Great Britain

[21] Appl. No.: 618,755

[22] Filed: Mar. 20, 1996

Related U.S. Application Data

[63] Continuation of PCT/GB94/02298, Oct. 20, 1994.

[30] Foreign Application Priority Data

Oct. 21, 1993 [GB] United Kingdom ............... 9321764

[51] Int. Cl.$^6$ ............... C12N 9/06; C12P 13/22
[52] U.S. Cl. ............... 435/191; 435/108; 435/189; 435/253.2; 435/872
[58] Field of Search ............... 435/189, 191, 435/108, 872, 253.2

[56] References Cited

U.S. PATENT DOCUMENTS

| | | | |
|---|---|---|---|
| 4,970,157 | 11/1990 | Hibino et al. | 435/189 |
| 5,015,582 | 5/1991 | Hibino et al. | 435/189 |
| 5,416,019 | 5/1995 | Leuchtenberger et al. | 435/108 |
| 5,420,023 | 5/1995 | Matsunaga et al. | 435/108 |

FOREIGN PATENT DOCUMENTS 0 215 414  3/1987  European Pat. Off.

OTHER PUBLICATIONS

Derwent Abstract 88–080328/12 JP63 32482 (Feb. 1988) Sagami Chem.
Biotech Abstract 88–07589 (GB2196333) (Apr. 1988) Allelix.
Derwent Abstract 90–235341/31 J02163081 (Jun. 1990) Central Glass KK.
Derwent Abstract 87–062508/09 J62019093 (Jan. 1987) Mitsui Toatsu Chem.
Biotech ABS 88–07115 "Biotechnol, Bioeng" (1988) 31,8, 834–40 Matsunaga et al.
Asano et al., "Novel Phenylalanine Dehydrogenases from *Sporosarcina ureae* and *Bacillus sphaericus*," *J. Biol. Chem.* 262:10346–10354 (1987).
Brearley et al., "Large–Scale Production and Purification of L–Phenylalanine Dehydrogenase from Nocardia SP.239," *Separations for Biotechnology 3, Third International Symposium of the Society of Chemical Industry*:79–85 (Sep. 1994).
de Boer et al. "Phenylalanine and Tyrosine Metabolism in the Facultative Methylotroph Nocardia sp. 239," *Arch. Microbiol.* 149:459–465 (1988).
de Boer et al., "Purification, Characterization and Regulation of a Monomeric L–Phenylalanine Dehydrogenase from the Facultative Methylotroph Nocardia sp. 239," *Arch. Microb.* 153:12–18 (1989).

*Primary Examiner*—Herbert J. Lilling
*Attorney, Agent, or Firm*—Sterne, Kessler, Goldstein & Fox P.L.L.C.

[57] ABSTRACT

A method for producing in culture phenylalanine dehydrogenase at yields of 50+ units of enzyme per litre of culture, one unit measured as the amount required to convert one micro-mole of phenylalanine to phenyl pyrovic acid at 25° C. and pH 10.8, in a growth medium comprising a nitrogen source, a buffer, phenylalanine or phenylpyruvic acid or a salt thereof at 20 mM and optionally a vitamin solution. Using phenylalanine at about 100 mM gives yields of phenylalanine dehydrogenase enzyme of 350+ units per liter of culture.

21 Claims, No Drawings

PHENYLALANINE DEHYDROGENASE PRODUCTION

This is a continuation of International application no. PCT/GB94/02298 filed on Oct. 20, 1994.

This invention relates to a growth medium for microorganisms capable of producing phenylalanine dehydrogenase, to a method of producing phenylalanine dehydrogenase, to a microorganism capable of producing phenylalanine dehydrogenase and to a method of purification of phenylalanine dehydrogenase.

Phenylalanine dehydrogenase (E.C. 1.4.1.-) catalyses the reversible conversion of L-phenylalanine to phenylpyruvate, with the concomitant reduction of $NAD^+$ to NADH, as shown by the equation;

*L-phenylalanine+$H_2O$+$NAD^+$=Phenylpyruvate+$NH_3$+$H^+$+NADH*

The enzyme has been demonstrated in a number of microorganisms, including; Brevibacterium sp. (Hummel W. et al. (1984). Arch. Microbiol., 137, 47–52), Rhodococcus sp. M4 (Hummel W. et al. (1986). Appl. Microbiol. Biotechnol., 25, 175–185), Sporosarcina ureae (Asano Y. and Nakazawa A. (1985). Agric. Biol. Chem., 49, 3631–3632), Bacillus sphaericus (Asano Y. et al. (1987). J. Biol. Chem., 262, 10346–10354), Bacillus badius (Asano Y. et al. (1987). Eur. J. Biochem., 168, 153–159), Rhodococcus maris K-18 (Misano H. et al. (1989). J. Bacteriol., 171, 30–36), Corynebacterium equi. EVA 5 (Evans C. T.et al. (1987). Biotechnology, 5, 818–823), Micrococcus luteus (Matsunaga T. et al. (1987). Appl. Microbiol. Biotechnol., 27, 11–14), Nocardia sp. 239 (Boer L. de and Dijkhuizen L. (1988). Arch. Microbiol., 149, 459–465) and Thermoactinomyces intermedius (Oshima T. et al. (1991). J. Bacteriol., 173, 3943–3948).

Phenylalanine dehydrogenase can be used for the synthesis of L-phenylalanine by the reductive amination of phenylpyruvic acid in the presence of ammonium ions and the reductive amination of several other α-ketocarboxylic acids to their corresponding aminocarboxylic acids as disclosed by U.S. Pat. No. 4,590,161. It can also be used to monitor levels of phenylalanine in biological fluids such as blood or sera (eg. Hummel W. et al. (1988) Anal. Biochem., 170, 397–401., Oshima T. et al. (1988). Anal. Letters, 21, 2205–2215., Wendel U. et al. (1990). Clin. Chim. Acta., 192, 165–170, Cooper A. et al. (1989). Analyt. Biochem., 183, 210–214 and Campbell R. S. et al. (1992). Clin. Chim. Acta. 210 pp 197–210. The quantification of serum phenylalanine is important in the diagnosis and treatment monitoring of phenylketonuria (PKU) and hyperphenylalaninaemia (HPA). Classical PKU arises from an autosomal recessive disorder which results in a deficiency or absence of the hepatic enzyme, phenylalanine hydroxylase (E.C. 1.14.16.1). Screening programmes for the detection of elevated serum phenylalanine levels in neonates permit such cases of HPA to be treated through dietary control. The condition and its causes is reviewed by Chang et al. (1991., J. Int. Fed. Clin. Chem., 3, 58–65).

The strain, originally called Streptomyces sp.239 (and containing the phenylalanine dehydrogenase described herein) was first described by Kato et al in 1974. The isolate was later renamed Nocardia sp. 239. The phenylalanine dehydrogenase from this strain was first described by de Boer et al (1988) Arch. Microbiol., 149, 459–465.

The enzyme has previously been extracted and purified (de Boer L., et al. (1989). Arch. Microbiol., 153, 12–18).

The growth medium used by de Boer for the cultivation of Nocardia sp. 239 was as follows:

| Component | g/L |
|---|---|
| $K_2HPO_4$ | 1.0 |
| $(NH_4)_2SO_4$ | 1.5 |
| $MgSO_4.7H_2O$ | 0.2 |
| L-phenylalanine | 1.65 | plus trace salts solution.

The above medium was sterilised prior to inoculation by autoclaving at 121° C., 15 psi for 20 minutes and was adjusted to pH 7.0. However, using this medium de Boer was only able to obtain rather low yields of phenylalanine dehydrogenase. It was also found that yield would not increase as the L-phenylalanine content was increased above an initial concentration of about 1 mM, and that above 2% (w/v) yield actually decreased. Objects of the invention include (i) enabling production of phenylalanine dehydrogenase at yields of more than 40 units per liter; (ii) providing a growth medium suitable for (i); (iii) providing a microorganism capable of producing phenylalanine dehydrogenase at yields of more than 40 units per litre; and (iv) providing an improved method of purification of phenylalanine dehydrogenase.

De Boer also describes purification of the enzyme using anion exchange chromatography and reports, in a single step process, an apparent 110-fold purification of crude enzyme product with 95% recovery. While the present invention also relates to enzyme activity and purification, direct comparison of improvements in the present invention over the prior published data by de Boer are extremely difficult because:

(a) De Boer's enzyme activity is based on measurement of the reductive amination of phenylpyruvate to phenylalanine, measured at pH 7.8 and 37° C. In the present invention, enzyme activity is based on the oxidative deamination of phenylalanine to phenylpyruvate (i.e. the reverse reaction), measured at pH 10.8 and 25° C., and (b) De Boer's enzyme levels are expressed as specific activities, in $nmol.min^{-1}.mg^{-1}$ of protein. In the present invention enzyme levels are expressed as units of activity per litre of culture, or units per gram of cell paste (wet weight), where one unit catalyses the deamination of 1 $\mu mol.min^{-1}$ substrate under the conditions outlined in (a).

Nevertheless, during the course of investigations in the present invention, the fermentation and purification processes described in the de Boer publication were repeated, and it is possible to compare our results using de Boer's methods with the results obtained using our own methods.

Despite repeated efforts, following de Boer's method, the inventors of this application have only been able to obtain, at best, a yield of enzyme of 40 units per litre. Following de Boer's methods we achieved a 25-fold purification of the enzyme, with maximum recovery of 82%. It is thus seen that the known growth media, methods and microorganisms only enable production of phenylalanine dehydrogenase at rather low yield and do not provide an efficient production procedure for crude enzyme from culture.

The present invention seeks to overcome or at least mitigate the problems in the prior art, resulting in improved yield of phenylalanine dehydrogenase from cell cultures and improved purification thereof.

In a first aspect the invention provides a method of producing phenylalanine dehydrogenase at yields of at least 50 units per litre, 1 unit being measured as described above, comprising culturing a microorganism capable of producing phenylalanine dehydrogenase in a growth medium for microorganisms capable of producing phenylalanine dehydrogenase comprising a nitrogen source, a buffer, phenylalanine or phenylpyruvic acid or a salt thereof, and optionally, a vitamin solution.

In a preferred embodiment the vitamin solution contains one or more vitamins selected from pyrodoxin, biotin, thiamine, nicotinic acid, riboflavin and mixtures thereof. If present, nicotinic acid is conveniently in an initial concentration of $10^{-2}$–$10^{-4}$ mg/L, the other vitamins conveniently at $10^{31\ 3}$–$10^{-5}$ mg/L. As will be appreciated by a person skilled in cell cultures of this sort it may also be convenient to include an anti-foaming agent. Further, while in the embodiments described below a nitrogen supplement is used, phenylalanine can act as a nitrogen source. Phenylpyruvate cannot act as a nitrogen source.

In another embodiment the growth medium also comprises a trace element solution, preferably containing one or more trace elements selected from salts of iron, zinc, cobalt, molybdenum, copper, boron, magnesium and mixtures thereof.

It is preferred that the phenylalanine or phenylpyruvic acid or salt thereof is present at between 20 mM and 1M, more preferably between 20 mM and 200 mM and most preferably between 50 mM and 150 mM; in a particular embodiment it is present at about 100 mM.

Using the method and growth medium of the invention it is possible to grow a culture of a microorganism capable of producing phenylalanine dehydrogenase, such as Nocardia sp. 239, so as to produce a yield of this enzyme of 50 or more units per litre of culture, one unit being measured as the amount of enzyme required to convert 1 micro-mole of phenylalanine to phenylpyruvic acid per minute at 25° C. and pH 10.8. This yield is significantly higher than previously obtainable, for example the 40 units per litre from comparable cultures using the known method of de Boer.

In another embodiment of the invention the growth medium comprises a nitrogen source, a buffer and phenylalanine or phenylpyruvic acid or a salt thereof at a concentration of 20 mM to 200 mM, preferably 50 mM to 150 mM and very preferably about 100 mM. In still another embodiment the growth medium comprises a nitrogen source, a buffer, phenylalanine or phenylpyruvic acid or a salt thereof and a trace element solution.

It is preferred that the method comprises maintaining the culture at 33° C.–38° C. It is further preferred that the method comprises maintaining the dissolved oxygen level of the culture above 40%.

In another preferred embodiment of the method, the pH of the culture is maintained at pH 6–8, more preferably at pH 7+0.5 and most preferably at pH 7+0.2.

In a particularly preferred embodiment the method comprises culturing Nocardia sp. 239, and very specifically a culture of a microorganism as deposited under NCIMB number 40590 on 12 Oct. 1993 or derived therefrom.

In a second aspect the invention provides a growth medium according to the first aspect.

In a third aspect the invention provides a microorganism capable of being grown in culture and producing phenylalanine dehydrogenase in an amount of at least 50 units per litre of culture, 1 unit being measured as defined above. In an embodiment of the invention the microorganism is capable of producing at least 100 units per litre of culture, and in a further embodiment at least 200 units per litre of culture. Preferably, the microorganism is Nocardia sp. 239.

A particularly preferred microorganism has been deposited under NCIMB number 40590 on 12 Oct. 1993 so this invention relates in a specific embodiment to this microorganism or to microorganism derived therefrom.

In a fourth aspect, the invention provides a method of purification of phenylalanine dehydrogenase from a homogenised cell supernatant containing phenylalanine dehydrogenase comprising the steps of:

1. loading the supernatant onto an affinity chromatography column pre-equilibrated with buffer at basic pH,
2. washing the column with the buffer to elute any unbound substances, and
3. eluting phenylalanine dehydrogenase using a solution of NADH in the buffer or by combination of increased pH and increased ionic strength. In an embodiment, the column is pre-equilibrated at pH 8–9 preferably pH 8.3–8.7.

Affinity columns that are of use in the present invention are those having sufficient affinity for phenylalanine dehydrogenase such that the enzyme binds to the column. The enzyme has greater affinity for NADH than for the column matrix, so use of NADH enables recovery of enzyme from the column matrix. Examples of suitable columns are those employing triazine dye—Sepharose matrices. In an embodiment hereinafter described the affinity column is a Procion Red He-3B/Sepharose column, preferably Sepharose 4B, 6B, CL-4B or CL-6B.

Preferably the method of purification further comprises the step of gel filtration of the purified product to remove NADH therefrom.

In an embodiment of the invention the elution is by an increased NaCl solution at pH 9+, preferably at about pH 10. In a preferred embodiment described below the elution is by a solution of NADH in the buffer, preferably at strength of 0–5 mM, more preferably about 1 mM.

The purification method of the invention enables a single step purification of phenylalanine dehydrogenase from the crude supernatant with an effective 30+ fold purification of the final product compared to the crude solution. In embodiments of the invention described below, 35+ fold purification is achieved.

There now follows some Examples of embodiments of the invention in which Nocardia sp. 239 was grown on a minimal salts medium containing the following:

| Component | g/L |
|---|---|
| $K_2HPO_4$ | 4.0 |
| $KH_2PO4$ | 1.0 |
| $NH_4Cl$ | 1.0 |
| $CaCl_2.2H_2O$ | 0.01 |
| $K_2SO_4$ | 2.6 |
| NaCl | 1.0 |
| L-phenylalanine | 16.5 (ie. 100 mM) |
| Mazu DF8005 antifoam | 0.5 ml/L |

The above medium was sterilised prior to inoculation by autoclaving at 121° C., 15 psi for 20 minutes and was adjusted to pH 7.0.

| | |
|---|---|
| 1M $MgCl_2.6H_2O$ | 1 ml/L |
| Trace element solution | 10 ml/L |
| Vitamin solution | 1 ml/L |

The trace salt and vitamin solutions were as follows:

Trace salts:

| Component | g/L |
| --- | --- |
| $FeCl_3 6H_2O$ | 3.90 |
| $ZnSO_4 H_2O$ | 0.58 |
| $CoCl_2 6H_2O$ | 1.00 |
| $Na_2MoO_4 2H_2O$ | 1.00 |
| $CuSO_4 5H_2O$ | 1.16 |
| $H_3BO_3$ | 0.30 |
| $MnSO_4 7H_2O$ | 0.72 |
| HCl (conc.) | 7.2 ml/L |
| Demin $H_2O$ | to 1000 ml |

Vitamin solution:

| Vitamin | mg/L |
| --- | --- |
| Pyridoxin | 0.125 |
| Biotin | 0.125 |
| Thiamine | 0.025 |
| Nicotinic acid | 1.875 |
| Riboflavin | 0.125 |

Enzyme activities are given as Units, defining one unit as 1 micro-mole of substrate (phenylalanine) deaminated per minute at 25° C. and pH 10.8.

EXAMPLE 1

Nocardia sp. 239 was grown in 100 ml of the minimal salts medium (as described above) in a 250 ml flask shaken at 200 rpm for 16–24 hours at 37° C. The resultant cell material was collected by centrifugation and assayed for phenylalanine dehydrogenase activity. The yield of enzyme was equivalent to 370 units/litre of culture.

EXAMPLE 2

The organism was grown as an 8 litre batch culture in a stainless steel reactor at 37° C. The culture was stirred at 400–700 rpm and the dissolved oxygen level was maintained above 40% by altering the air flow rate and impeller speed. The pH of the medium was controlled at pH 7.0+0.2 and the vessel was inoculated with a 200 ml seed culture prepared in the same medium and incubated for 16–24 hours, as described in Example 1. The 8 litre culture was incubated for 18 hours (optical density 600 nm=21) and was harvested by centrifugation. The enzyme yield was 360 units/litre.

EXAMPLE 3

Frozen ampules of Nocardia sp. 239 containing 29 ml (7.2x108 CFU/ml) were used to inoculate a 20 litre seed culture which was grown in a stainless steel reactor under conditions similar to those described in Example 2.

A 400 litre vessel containing 400 litres of the minimal medium was seeded with the 20 litre seed culture, which was in mid log phase (OD at 600 nm of 12–14). Growth was continued at 37° C. and a controlled pH of 7.0+0.2 with aeration at 200 litres of air per minute and stirred at 200 rpm until the percentage carbon dioxide in the exhaust gases began to fall. The duration of the culture was 18.5 hours and the final optical density at 600 nm was 16.0. The culture was cooled to 8°–10° C., transferred under top pressure to a holding vessel and harvested using a Westfalia centrifuge run at 50–60 litres/hour.

The final enzyme yield was 140,000 units from a total of 14.0 Kg of wet cell paste, equivalent to 350 units/litre of culture.

EXAMPLE 4

All purification procedures were performed at 10° C. or less. Phenylalanine dehydrogenase was purified in a single step from homogenised cell supernatant (crude extract) using a Procion Red HE-3B/Sepharose CL-4B column.

The Procion dye was coupled to the support matrix by the method of Atkinson et al. ((1981). Biochem. Soc. Trans., 9, 290–293) and the level of dye substitution was determined to be 3.15 mg of dye per millilitre of gel, using acid-hydrolysed samples. Sepharose 4B, 6B and CL-6B were all found to bind similar levels of dye and were equally effective as purification matrices.

The optimum binding conditions were found to be 50 mM Tris-HCl buffer, pH 8.5. The protease inhibitor, phenyl-methanesulphonyl fluoride (PMSF) was routinely added to all buffers at 0.1 mM. The maximum binding capacity was found to be 4.0 units of phenylalanine per millilitre of the matrix. The enzyme was eluted from the column by the inclusion of 1 mM NADH in the buffer, or by a combination of increased pH and ionic strength (eg. 500 mM NaCl and pH 10.0).

A 1 ml disposable plastic column was packed with 1 ml of the Procion matrix and equilibrated with 50 mM Tris-HCl pH 8.5 0.1 mM PMSF. A cell suspension of Nocardia sp. 239 was disrupted by sonication and the cell debris removed by centrifugation to yield a cell extract containing 0.10 units per mg of protein. A total of 2 units of enzyme were loaded to the 1 ml column and, after washing to remove unbound substances, were eluted with 1 mM NADH. The purification achieved an effective 40-fold purification over crude (final specific activity=4.0 U/mg) and a recovery of 78%.

EXAMPLE 5

A total of 30 g of wet cells were suspended in buffer and disrupted by sonication. The cell debris was removed by centrifugation and the crude extract (185 units, 0.09 U/mg) was loaded onto a 100 ml column (46 mm diameter, 61 mm high) packed with the Procion matrix. The column was run at 300 ml/hour and produced a recovery of 75%, with a 38-fold purification (3.42 U/mg) over crude.

EXAMPLE 6

Using material from the 400 litre culture (Example 3), cells were suspended in buffer and disrupted using an APV Manton restricted orifice homogeniser, operated at 8000 psi. The cell debris was removed by centrifugation and the crude extract (5000 units, 0.10 U/mg) was applied to a 2.4 litre Procion column (140 mm diameter, 155 mm high) which was run at 4.8 litres/hour (max. 8.4 litres/hour). The enzyme was eluted with 1 mM NADH and achieved a purification of 39 fold (3.9 U/mg) and a recovery of 65%.

These Examples may be compared with the following Comparative Examples.

COMPARATIVE EXAMPLE 1

Nocardia sp. 239 was grown in 100 ml of the original chemically defined medium (as described above with reference to de Boer) in a 250 ml flask shaken at 200 rpm for 16–24 hours 37° C. The cell material was harvested by centrifugation and assayed for phenylalanine dehydrogenase activity. The final enzyme level was 35 units/litre of culture.

COMPARATIVE EXAMPLE 2

The organism was grown as an 8 litre batch culture in a stainless steel reactor at 37° C. The culture was stirred at 500 rpm and the dissolved oxygen level was maintained above 40% by altering the air flow rate. The pH of the medium was controlled at pH 7.0+0.2 and the vessel was inoculated with a 200 ml seed culture prepared in the same medium and incubated for 16–24 hours, as described in comparative Example 1. The 8 litre culture was incubated for 20 hours (optical density at 600 nm=2.7) and was harvested by centrifugation in 1 litre pots. The enzyme yield was 37 units/litre.

COMPARATIVE EXAMPLE 3

A 1 litre pre-seed of Nocardia sp. 239 was prepared at 37° C. in a shake flask and was used to inoculate a 25 litre seed culture grown in a stainless steel vessel under conditions similar to those described in comparative Example 2 for an 8 litre culture.

A 400 litre vessel containing the minimal medium was inoculated with the 25 litre seed culture. Growth was continued at 37° C. and a controlled pH of 7.0+0.2 with aeration at 200 litres of air per minute and stirred at 200 rpm until the percentage carbon dioxide in the exhaust gases began to fall. The duration of the culture was 16.5 hours and the final optical density at 600 nm was 2.2. The culture was cooled to 8°–10° C., transferred under top pressure to a holding vessel and harvested using a Westfalier centrifuge run at 50–60 litre/hour.

The final enzyme yield was 16,000 units from a total of 2.36 Kg of wet cell paste, equivalent to 40 units/litre of culture.

The invention thus provides improved production of phenylalanine dehydrogenase from e.g. Nocardia sp. 239, in a quality and quantity suitable for the determination of phenylalanine in biological fluids. The enzyme has been purified from crude cell extracts in a single column affinity chromatography step using a method that is simple, reproducible and well suited to scale-up.

We claim:

1. A method of producing phenylalanine dehydrogenase at yields of at least 50 units per litre, one unit being measured as the amount required to convert one micro-mole of phenylalanine to phenylpyruvic acid at 25° C. and pH 10.8, comprising culturing a microorganism capable of producing phenylalanine dehydrogenase in a growth medium comprising:
   1) a nitrogen source,
   2) a buffer, and
   3) phenylalanine or phenylpyruvic acid or a salt thereof at a concentration of at least 20 mM.

2. A method according to claim 1 wherein the growth medium additionally comprises a vitamin solution containing one or more vitamins selected from pyridoxin, biotin, thiamine, nicotinic acid, riboflavin and mixtures thereof.

3. A method according to claim 1 further comprising a trace element solution comprising one or more trace elements selected from salts of iron, zinc, cobalt, molybdenum, copper, boron, magnesium and mixtures thereof.

4. A method of producing phenylalanine dehydrogenase at yields of at least 50 units per litre, one unit being measured as the amount required to convert one micro-mole of phenylalanine to phenylpyruvic acid at 25° C. and pH 10.8, comprising culturing a microorganism capable of producing phenylalanine dehydrogenase in a growth medium comprising:
   1) a nitrogen source,
   2) a buffer,
   3) phenylalanine or phenylpyruvic acid or a salt thereof, and
   4) a trace element solution.

5. A method according to claim 4 wherein the trace element solution contains one or more trace elements selected from salts of iron, zinc, cobalt, molybdenum, copper, boron, magnesium and mixtures thereof.

6. A method according to claim 1 in which component 3 is present at between 20 mM and 1M.

7. A method of producing phenylalanine dehydrogenase at yields of at least 50 units per litre, one unit being measured as the amount required to convert one micro-mole of phenylalanine to phenylpyruvic acid at 25° C. and pH 10.8, comprising culturing a microorganism capable of producing phenylalanine dehydrogenase in a growth medium comprising:
   1) a nitrogen source
   2) a buffer, and
   3) phenylalanine or phenylpyruvic acid at a concentration of 20 mM to 200 mM.

8. A method according to claim 1 comprising component 3 at about 100 mM.

9. A method according to claim 1 in which the microorganism is Nocardia sp. 239.

10. A method according to claim 1 for producing phenylalanine dehydrogenase at yields of at least 100 units per litre.

11. A method according to claim 10 comprising maintaining the culture at 33° C.–38° C.

12. A method according to claim 10 comprising maintaining the dissolved oxygen level of the culture above 40%.

13. A method according to claim 10 comprising maintaining the pH at 6–8.

14. A method according to claim 10 in which the microorganism is Nocardia.

15. A method according to claim 1, wherein said microorganism is capable of being grown in culture and producing phenylalanine dehydrogenase in an amount of at least 50 units per litre of culture, one unit being measured as the amount required to convert one micro-mole of phenylalanine to phenylpyruvic acid at 25° C. and pH 10.8.

16. The method according to claim 15, wherein said microorganism is as deposited under NCIMB 40590, or is derived therefrom.

17. A method according to claim 1 in which component 3 is present at between 20 mM and 200 mM.

18. A method according to claim 1 in which component 3 is present at between 50 mM to 150 mM.

19. A method according to claim 1 for producing phenylalanine dehydrogenase at yields of at least 200 units per litre.

20. A method according to claim 10 comprising maintaining the pH at 6±0.5.

21. A method according to claim 10 comprising maintaining the pH at 7±0.2.

* * * * *